United States Patent [19]

Cambio, Jr.

[11] Patent Number: 4,500,480

[45] Date of Patent: Feb. 19, 1985

[54] PEDIATRIC CARTRIDGE HUMIDIFIER

[75] Inventor: Orlando D. Cambio, Jr., Bristol, Wis.

[73] Assignee: Respiratory Care, Inc., Arlington Heights, Ill.

[21] Appl. No.: 549,075

[22] Filed: Nov. 7, 1983

Related U.S. Application Data

[63] Continuation of Ser. No. 410,626, Aug. 23, 1982, abandoned.

[51] Int. Cl.[3] .................... B01F 3/04; A61M 15/00

[52] U.S. Cl. .................... 261/104; 128/200.11; 128/202.22; 128/203.19; 128/204.13; 137/393; 219/274; 261/72 R; 261/142; 261/154; 261/DIG. 65

[58] Field of Search .................... 261/66, 67, 72 R, 104, 261/107, 142, 152-156, DIG. 65; 128/200.11, 203.19, 204.13, 202.22; 137/391, 393, 568; 219/271-276, 385, 535

[56] References Cited

U.S. PATENT DOCUMENTS

| | | | |
|---|---|---|---|
| 3,178,159 | 4/1965 | Johnson | 261/142 X |
| 3,385,578 | 5/1968 | Porter | 261/DIG. 65 |
| 3,387,607 | 6/1968 | Gauthier et al. | 261/DIG. 65 |
| 3,744,722 | 7/1973 | Burns | 261/DIG. 65 |
| 3,771,721 | 11/1973 | Van Amerongen | 261/DIG. 65 |
| 3,805,780 | 4/1974 | Cramer et al. | 137/568 X |
| 3,864,440 | 2/1975 | Giocoechea | 261/DIG. 65 |
| 3,874,379 | 4/1975 | Enfield | 261/DIG. 65 |
| 4,010,748 | 3/1977 | Dobritz | 261/DIG. 65 |
| 4,110,419 | 8/1978 | Miller | 261/142 |
| 4,148,334 | 4/1979 | Richards | 137/393 X |
| 4,172,105 | 10/1979 | Miller et al. | 261/66 |
| 4,178,334 | 12/1979 | Miller | 219/275 X |
| 4,195,044 | 3/1980 | Miller | 261/104 X |
| 4,198,969 | 4/1980 | Virag | 261/72 R X |
| 4,366,105 | 12/1982 | Nowacki | 128/204.13 X |
| 4,450,118 | 5/1984 | Tuin | 261/DIG. 65 |

*Primary Examiner*—Richard L. Chiesa

*Attorney, Agent, or Firm*—Allegretti, Newitt, Witcoff & McAndrews, Ltd.

[57] ABSTRACT

A previously disclosed cartridge type humidifier apparatus including a separate heater module with a cylindrical opening for replaceably receiving therein disposable cylindrical humidifier cartridge modules, having a housing containing a replenishable water supply is employed as a water supply source for reproducing an aerosol with an oxygen supply for pediatric inhalation therapy. The cartridge modules each have a tubular metal main body adapted for a sliding fit within a complimentary tubular wall heater. The metal tubular body has a rigid plastic top and bottom end portions. The top end portions is a cap with a center axial gas inlet tube and a separate transverse gas delivery tube, the cap forming a closed air space over a pool of humidified liquid each cartridge includes an absorption column preferably of this cylindrical tube form which is adapted to lie closely adjacent and draw water up along the cartridge cylindrical metal body which insures as a evaporating surface when heated by the heater modules. The gas to be humidified is dispersed within a hollow chamber formed between the gas inlet pipe projecting concentrically into the cartridge and the radially spaced wall of the main cartridge body and the absorption column. Water is fed to the humidifier from the bottom of a bottle of sterile water through a water inlet tube. An air flow tube is connected to the plastic top end portion. Check valves are positioned in both the water inlet and air flow lines.

12 Claims, 3 Drawing Figures

PEDIATRIC CARTRIDGE HUMIDIFIER

This is a continuation of application Ser. No. 410,626, filed Aug. 23, 1982, and now abandoned.

BACKGROUND OF THE INVENTION

The present invention relates to a modification of an inhalation therapy device for use with a patient ventilator.

U.S. Pat. No. 3,771,721 issued Nov. 13, 1973, relates to inhalation therapy in the medical art of treating with oxygen or a mixture of oxygen and air having a high moisture content. Several classes of devices including atomizers and humidifiers are adapted for such treatments. With respect to atomizers and nebulizers as they are frequently called, a heretofore known system for inhalation therapy comprises a container for pure water which has means enabling operation of the container in one of several modes.

U.S. Pat. No. 4,110,419 issued Aug. 29, 1978, and U.S. Pat. No. 4,172,105 issued Oct. 23, 1979, relate to a cartridge type humidifier apparatus that includes a separate heater module with a cylindrical opening for replaceably receiving therein disposable cylindrical humidifier cartridge modules. The cartridge modules each have a tubular metal main body adapted for a sliding fit within a complimentary tubular walled heater. The metal tubular body has a rigid plastic top and bottom end portions with a separate transverse gas delivery pipe, the cap forming a closed air space over a pool of humidifying liquid. The gas to be humidified is dispersed within a hollow chamber formed between the gas inlet pipe projecting concentrally into the cartridge and the radially spaced wall of the main cartridge body and absorption column. The inlet tube terminates above the water. The subject matter of the above patents are incorporated herein by reference. The instant device is a modification of the disclosure in these patents to provide an improved cartridge humidifier.

SUMMARY OF THE INVENTION

The present invention relates to a waterfeed circuit for delivering water from a reservoir to a humidifying apparatus connected within a ventilation system wherein the ventilation system produces a cycling pressure within the humidifier. The circuit maintains a constant water volume within the humidifier while isolating the compliance of the reservoir from the system. The circuit includes a level sensing tube positioned in the humidification apparatus. The top of the level sensing tube is connected by means of an air flow conduit having a check valve positioned therein that connects to an air space in the top of the reservoir of an aseptic liquid. Water is fed to the humidifying apparatus by means of a conduit connecting the reservoir with the cylindrical cartridge of the apparatus. A check valve is positioned in this conduit.

Although this system can be used for adult as well as pediatric humidification, to simplify the discussion, this apparatus will be described as a modification of U.S. Pat. No. 4,110,419 and, more specifically, U.S. Pat. No. 4,172,105 that provide breathable inhaled gases that are moisture laden with a large quantity of water for pediatric use. The elements of the device that are not mentioned above are identical with the structure shown in U.S. Pat. No. 4,172,105.

DETAILED DESCRIPTION OF THE PREFERRED EMBODIMENT

Since the instant application covers the modification of high volume disposable and semi-disposable cartridge humidifiers with self-contained cartridge sterilizing means disclosed and claimed in U.S. Pat. No. 4,172,105 and U.S. Pat. No. 4,110,419, only the essential portions of this modified apparatus will be discussed in detail.

Figure 1:
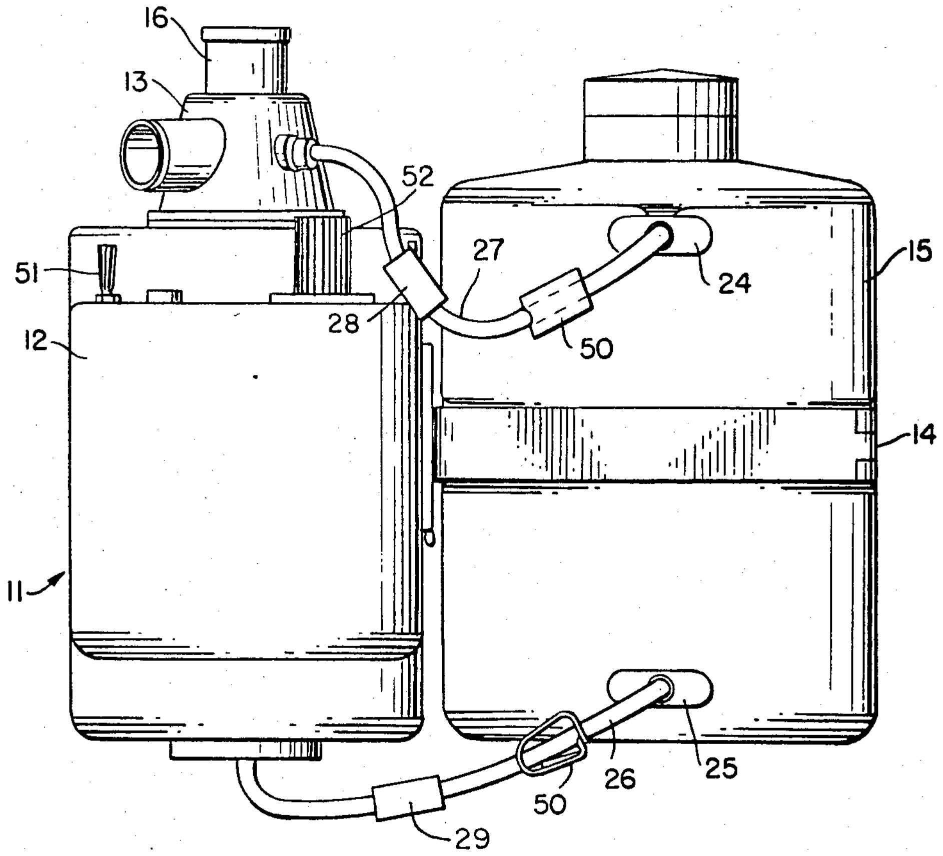
FIG. 1 is a perspective view of the assembled humidifying apparatus according to one form of the invention.
Figure 2:
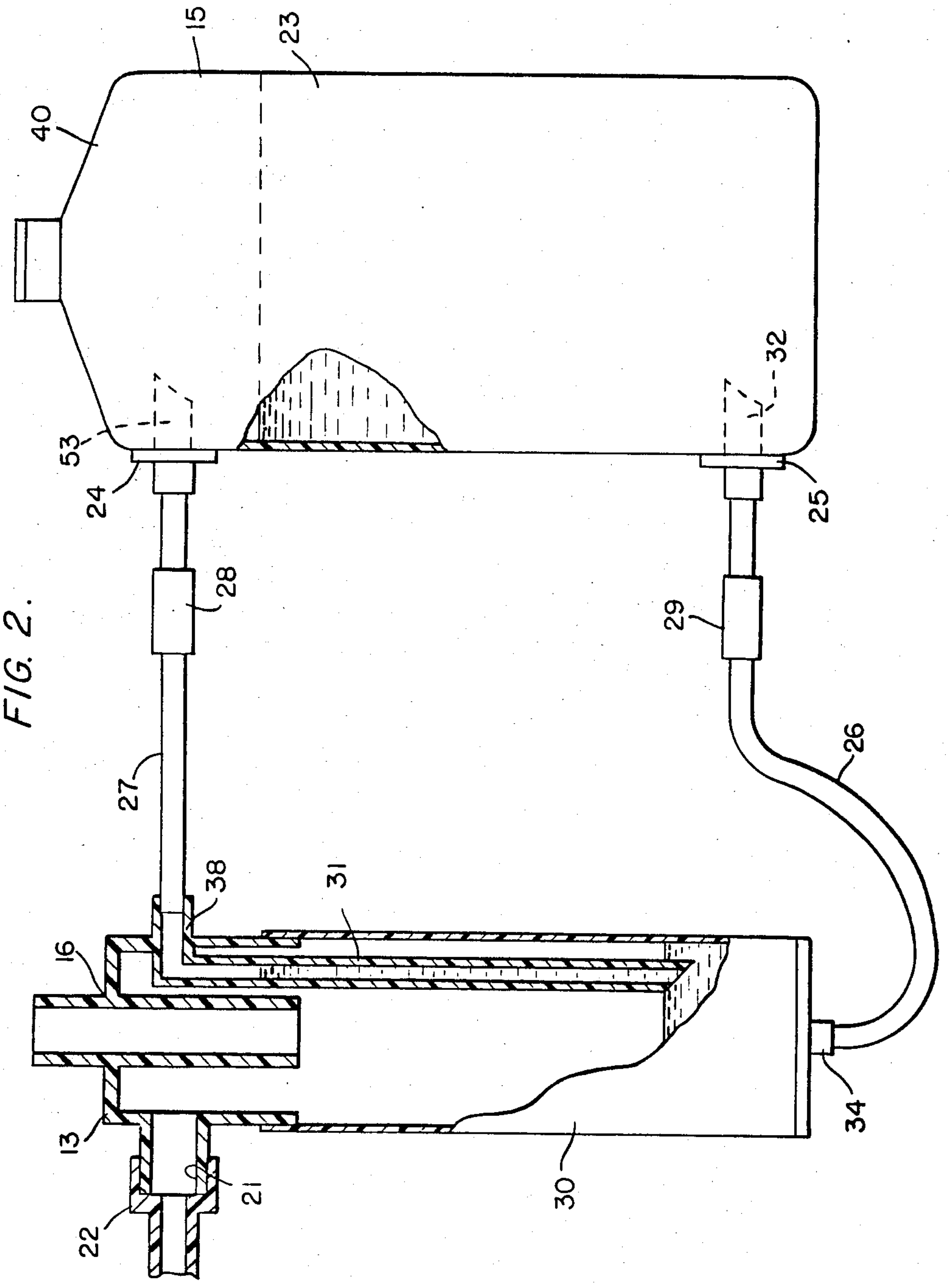
FIG. 2 is another perspective view of the invention with a portion of the structure shown in cross section.

Reference is made to FIGS. 1 and 2 wherein the modification of the humidifier and nebulizer assembly is generally indicated by the member 11. The assembly comprises a combined heater cartridge supporting means 12 with a disposable or semi-disposable cartridge module 30 as shown in FIG. 2, preferably with a nonmetallic top body cap 13. The details of the heater and cartridge supporting module are described in detail in U.S. Pat. No. 4,110,419 and will not be repeated here.

Additionally, the supporting means 12 is provided with a bracket means 14 to support therewith a suitably prepared water supply thermoplastic bottle 15 with which the system hereof is designed to work as aseptically prefilled bottles known as Concha ® preferably the Concha ® 1500 (1500 ml) marketed by Respiratory Care, Inc., of Arlington Heights, Ill. The bottle is provided with breachable seals 24 and 25 for accommodating piercing members 32 and 53 in a manner shown in FIG. 2. The cap 13 is provided with a gas delivery port 21. A flexible tubing 22 is shown fragmentarily in connection with a gas delivery port 21 and is adapted to deliver the treated gas to the patient. A liquid water bottle reservoir means shown in the drawing is preferably the aforesaid Concha ® unit placed in upright position adjacent to the supporting means 12. The unit is a disposable sealed plastic container of aseptic water. The container comprises a principal chamber 23 which is shown in the drawing as provided with breachable seals 24 and 25 and connecting tubes 26 and 27. The essential feature of this invention resides in the method of connecting the bottle 15 with the humidifier cartridge 30 and in the elements designed to control the water level in the humidifier cartridge 30.

The tube 26 is connected to the bottom of the bottle 15 through the connector 25 having the piercing member 32. The other end of the tube 26 is connected through the connector 34 to the bottom of the humidifier cartridge 30. The tube 27 is connected to the top of the bottle through the connector 24 having a piercing member 53 attached thereto. The other end of the tube 27 is connected through the connector 38 to the level sensing tube 31 positioned in the humidifier cartridge 30.

Figure 3:
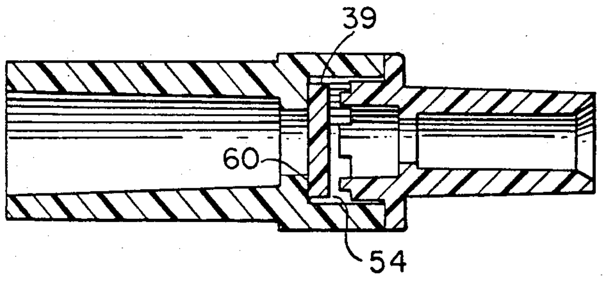
FIG. 3 is a cross sectional view of the valve and stop elements of the structure in more detail.

FIG. 3 is a cross-sectional view of the check valves 28 and 29 in FIGS. 1 and 2. The valves consist of an elastomeric disk 39 that moves between positions 54 and 60. When the disk is in position 54, water can flow through the conduit 26 and air can flow through the conduit 27. When the disk is in position 60, the valve is closed and water cannot flow through the conduit 26 and air cannot flow through the conduit 27.

In operation of the system the check valves 28 and 29 control the flow of the water from the reservoir 15 through the humidifier cartridge 30 and the air from the air space 40 to the level sensing tube 31. Referring again to FIG. 1, clip means 50 are positioned onto 26 and 27. The apparatus includes an on and off switch 51 and a controllable member 52.

In operation of the system when the humidifier cartridge is first connected, water will flow by gravity from the bottle 15 to the humidifier cartridge 30 through the connectors 25 and 34. The water will rise in the humidifier cartridge 30 and will eventually close off the air supply to the level sensing tube 31.

The water will continue to rise in the level sensing tube 31 and create a negative pressure in the bottle air space 40. At equilibrium the level in the sensing tube 31 will be equal to the level in the bottle 15. The negative pressure in the bottle will equal the hydrostatic pressure equivalent to the difference in levels between the water in the bottle and the water in the humidifier cartridge 30.

When used for noncycling, continuous flow applications evaporation will cause a drop in the level of water in the humidifier cartridge 30 and will expose the bottom of the level sensing tube 31 to air. Some of the water in the sensing tube will drain and be replaced by air from within the humidifier cartridge 30. This will create an imbalance so that water will flow from the bottle 15 through the connector 25, tube 26, and connector 34 into the humidifier cartridge 30. The cycle will repeat as the water in the humidifier cartridge is used up and a constant water level will be maintained.

During the inspiration portion of a ventilator cycle, the pressure in the humidifier cartridge 30 will increase relative to the reservoir 15 and if the water level in the cartridge 30 is above the control level, the water will be forced into conduit 27 and check valve 28 will open. If the water level in the cartridge 30 is below the control level, air will move through the conduit 27 and into the reservoir 15. Water forced into conduit 26 will cause check valve 29 to close during the expiration portion of the cycle, the pressure in the humidifier cartridge 30 will decrease substantially relative to the reservoir 15. This will cause check valve 28 to close and check valve 29 to open and water to move from the reservoir 15 through conduit 26 into cartridge 30. The system will constantly try to reach equilibrium. The pressure in the reservoir 15 will increase until the air supply is cut off and then will decrease until the air supply is reopened. The check valve 29 in conduit 26 prevents water from being forced back into the bottle during inspiration and allows water to flow during expiration. The check valve 28 in conduit 27 prevents the pressure in the reservoir 15 from being relieved during expiration but also allows the air or excess water to be forced through conduit 27 during inspiration. Another fact is that a fairly constant water level is maintained and the compliance (expansion and contraction of the reservoir) is significantly reduced.

While one preferred embodiment has been illustrated and described in detail it is apparent that other modifications and changes may be made by those skilled in the art without departing from the inventive spirit thereof. Reference should be made to the appending claims for the inventive scope of this invention.

What is claimed is:

1. A feeder circuit for delivering a liquid from a reservoir to a cartridge module, said cartridge module having a top portion and a bottom portion, comprising, in combination:

support means for securing said reservoir in fixed relationship to said cartridge module;

a first conduit connecting said bottom portion of said cartridge module to said reservoir;

first valve means interconnected in said first conduit for permitting passage of fluid from said reservoir to said cartridge module;

a fluid level sensing tube extending into said cartridge module through said top portion and extending therein towards said bottom portion, said fluid level sensing tube having a first end external to said cartridge module and a second end within said cartridge module, said second end of said fluid level sensing tube substantially defining a fluid control level within said cartridge module;

a second conduit connecting said first end of said fluid level sensing tube and said reservoir; and second valve means interconnection in said second conduit for permitting passage of fluid from said cartridge module to said reservoir;

said support means, said first conduit, said first valve means, said fluid level sensing tube, said second conduit, and said second valve means cooperatively defining fluid level means for maintaining the level of said liquid within said cartridge module substantially at said fluid control level.

2. A feeder circuit as claimed in claim 1 wherein said first and second conduits include a connector having a piercing member adapted to puncture said reservoir.

3. A feeder circuit as claimed in claim 1 wherein said cartridge module includes a top cap substantially closing said top portion, said fluid level sensing tube extending through said top cap.

4. A feeder circuit as claimed in claim 3 wherein said cartridge module further includes a bottom cap substantially closing said bottom portion, said first conduit interconnecting with said bottom cap.

5. A system for providing a moisturized gas comprising, in combination:

a reservoir holding a moisturizing liquid;

a cartridge module having an upper portion and a lower portion, said cartridge module being adapted to hold a quantity of said moisturizing liquid, said cartridge module further including a gas inlet port and a gas delivery port;

support means for securing said reservoir relative to said cartridge module;

means for producing a gas flow through said gas inlet port, said cartridge module, and said gas delivery port as to produce said moisturized gas; and a feeder circuit for feeding said moisturizing liquid from said reservoir to said cartridge module so as to maintain a substantially constant liquid level therein;

said feeder circuit including (i) first conduit means for interconnecting said lower portion of said cartridge module and said reservoir, said first conduit means including first valve means therein for passing fluid substantially solely from said reservoir to said cartridge module, (ii) a fluid level sensing tube within said cartridge module having a terminus therein defining a liquid control level, a portion of said fluid level sensing tube extending externally of said cartridge module, (iii) second conduit means for interconnecting said portion of said fluid level sensing tube and said reservoir, said second conduit means including second valve means therein for passing fluid substantially solely from said cartridge module to said reservoir.

6. A system as claimed in claim 5 wherein said first and second conduit means include a connector having a piercing member adapted to puncture said reservoir.

7. A system as claimed in claim 5 further comprising heater means for heating said cartridge module, said heater means being adapted to receive said cartridge module in heat-transfer relationship.

8. A system as claimed in claim 5 wherein said cartridge module includes an upper cap substantially closing said upper portion, said fluid level sensing tube extending through said top cap.

9. A system as claimed in claim 8 wherein said cartridge module further includes a lower cap substantially closing said lower portion, said first conduit interconnecting with said lower cap.

10. A cartridge humidifying apparatus for humidifying and heating a breathable gas such as oxygen supplemented air to be inhaled by a patient undergoing inhalation therapy comprising:

(a) a humidifier cartridge module means embodying a tubular cartridge main body portion with an inner peripheral wall;

(b) said cartridge module means including an upper end portion with cap means attached to said main body;

(c) said humidifier cartridge module means including a lower end portion terminating in a transverse wall and adapted and constructed to retain a humidifying liquid, said transverse wall having liquid inlet means adapted to be fluidly connected via conduit means with a liquid outlet means of an external liquid source;

(d) said humidifier cartridge module means further comprising liquid absorption means including an open center generally tubular liquid-absorption column member with an inner-peripheral face constituting an evaporating surface for humidifying liquid disposed generally contiguously and coextensive with a substantial part of said cartridge main body and said lower end portion adapted and constructed to be wetted directly by the humidifying liquid when liquid is in said lower end portion, and to convey by capillary action the liquid upwardly of said absorption means and onto said evaporating surface;

(e) a fluid level sensing tube positioned in said humidifier cartridge module adjacent to said central tubular liquid absorption column and extending from near the bottom of said humidifier cartridge module to said upper end portion cap means;

(f) said upper end portion cap means of said humidifier cartridge module means of paragraph (b) together with a portion of said main body providing an air space above the humidifying liquid level in said lower end portion of said paragraph (c) when liquid is in said lower end portion;

(g) said cap means including a breathable gas inlet feed pipe for directing gas to be humidified into said module and terminating in said main body;

(h) said cap means further including an outwardly projecting humidified breathable gas outlet delivery pipe in fluid commnuication with said air space, said delivery pipe adapted to be connected with an output delivery tube;

(i) a disposable reservoir of aseptic liquid sealed therein, said disposable reservoir having a liquid outlet pipe, means for detachably mounting said reservoir externally of said module means and liquid inlet means adapted to fluidly connect via conduit means with said liquid outlet means of said external reservoir of aseptic liquid with said module means wherein said conduit means comprises a first tubular member having a check valve positioned therein, one end of said tubular member connected to the liquid outlet of said reservoir, the other end of said tubular member connecting to the inlet of said module, a second tubular conduit having a check valve therein, one end of said second tubular conduit connecting said level sensing tube in said upper end portion cap means, the other end of said second tubular member connecting through said check valve to the upper portion of said reservoir of aseptic liquid.

11. The apparatus according to claim 10 wherein the check valve in said first conduit is of sufficient size to close said conduit and prevent back flow of water from said module to said reservoir.

12. The apparatus according to claim 10 wherein the check valve in said second conduit is of sufficient size to close said conduit and prevent back flow of air from said reservoir to the upper end portion cap means of said module.

* * * * *